US012569250B2

(12) United States Patent　　　　　(10) Patent No.:　US 12,569,250 B2
Kollar et al.　　　　　　　　　　　　　　(45) Date of Patent:　　Mar. 10, 2026

(54) SYSTEMS AND METHODS FOR CLAMPING AND STAPLING TO A PRESSURE BY A SURGICAL STAPLING INSTRUMENT

(71) Applicant: Covidien LP, Mansfield, MA (US)

(72) Inventors: Charles R. Kollar, Washington, DC (US); Alexander J. Hart, Tolland, CT (US); David E. Valentine, Jr., Hamden, CT (US); Haley E. Strassner, Hamden, CT (US)

(73) Assignee: Covidien LP, Mansfield, MA (US)

( * ) Notice: Subject to any disclaimer, the term of this patent is extended or adjusted under 35 U.S.C. 154(b) by 746 days.

(21) Appl. No.: 17/323,118

(22) Filed: May 18, 2021

(65) Prior Publication Data

US 2022/0015766 A1　　Jan. 20, 2022

Related U.S. Application Data

(60) Provisional application No. 63/052,571, filed on Jul. 16, 2020.

(51) Int. Cl.
　　A61B 17/072　　　(2006.01)
　　A61B 17/115　　　(2006.01)
　　　　　　(Continued)

(52) U.S. Cl.
　　CPC . A61B 17/1155 (2013.01); *A61B 2017/00119* (2013.01); *A61B 2017/07257* (2013.01);
　　　　　　(Continued)

(58) Field of Classification Search
　　CPC .................... A61B 17/1155; A61B 2017/0725
　　See application file for complete search history.

(56) References Cited

U.S. PATENT DOCUMENTS 7,407,075 B2 * 8/2008 Holsten ................ A61B 17/115
　　　　　　　　　　　　　　　　　　　　　　　227/19
8,028,885 B2 * 10/2011 Smith .................... A61B 90/03
　　　　　　　　　　　　　　　　　　　　　　　227/176.1
(Continued)

FOREIGN PATENT DOCUMENTS

CN　　　106028964 A　　10/2016
CN　　　108472087 A　　　8/2018
　　　　　　(Continued)

OTHER PUBLICATIONS

Extended European Search Report dated Dec. 6, 2021 corresponding to counterpart Patent Application EP 21185659.6.

(Continued)

*Primary Examiner* — Gloria R Weeks

(57) ABSTRACT

A surgical stapling instrument includes an anvil assembly, a reload assembly, an adapter assembly, a processor, and a memory. When clamping to a target pressure, the instructions cause the surgical stapling instrument to advance the anvil assembly in relation to a staple cartridge supported on the reload assembly to a first position to define a first tissue gap within a predetermined acceptable range of tissue gaps, measure a first force of tissue compression of tissue clamped within the first tissue gap with the anvil assembly in the first position, and enter a firing mode of the surgical stapling instrument if the first force of tissue compression is within a predetermined acceptable range of tissue compression.

14 Claims, 6 Drawing Sheets

(51) Int. Cl.
   *A61B 17/00* (2006.01)
   *A61B 90/00* (2016.01)
(52) U.S. Cl.
   CPC ............... *A61B 2017/07271* (2013.01); *A61B 2090/064* (2016.02); *A61B 2562/0261* (2013.01)

(56) References Cited

U.S. PATENT DOCUMENTS

| | | | | |
|---|---|---|---|---|
| 8,066,167 | B2 * | 11/2011 | Measamer | A61B 90/06 |
| | | | | 227/179.1 |
| 9,724,094 | B2 * | 8/2017 | Baber | H02H 3/207 |
| 9,808,246 | B2 * | 11/2017 | Shelton, IV | A61B 17/07207 |
| 10,856,867 | B2 * | 12/2020 | Shelton, IV | A61B 17/105 |
| 2007/0179408 | A1 | 8/2007 | Soltz | |
| 2013/0110088 | A1 | 5/2013 | Wenchell | |
| 2016/0220150 | A1 | 8/2016 | Sharonov | |
| 2019/0090877 | A1 * | 3/2019 | Fox | A61B 17/1155 |
| 2019/0200996 | A1 * | 7/2019 | Shelton, IV | A61B 90/361 |
| 2019/0200997 | A1 * | 7/2019 | Shelton, IV | G16H 20/40 |
| 2019/0200998 | A1 * | 7/2019 | Shelton, IV | A61B 90/361 |
| 2019/0261991 | A1 * | 8/2019 | Beckman | A61B 17/115 |
| 2019/0343517 | A1 | 11/2019 | Zemlok et al. | |
| 2020/0015820 | A1 | 1/2020 | Contini et al. | |
| 2021/0275053 | A1 * | 9/2021 | Shelton, IV | A61B 17/07207 |

FOREIGN PATENT DOCUMENTS

| | | |
|---|---|---|
| CN | 108852443 A | 11/2018 |
| EP | 1728475 A2 | 12/2006 |
| JP | 2019513048 A | 5/2019 |

OTHER PUBLICATIONS

Office Action for Japanese Patent Application No. 2021-111271 mailed Jan. 9, 2025, 7 pages.
Office Action for Chinese Patent Application No. 202110766622.5 mailed Jun. 21, 2025, 28 pages.
Notice of Allowance for Japanese Patent Application No. 2021-111271 mailed Apr. 22, 2025, 5 pages.

* cited by examiner

S0- Start of Low Speed Stapling

S1- End of Staple Detection Zone

S2- Minimum Staple Position

S3- Maximum Staple Position

Staple Force (lbs)

S0          S1          S2   S3

Staple Position

SYSTEMS AND METHODS FOR CLAMPING AND STAPLING TO A PRESSURE BY A SURGICAL STAPLING INSTRUMENT

CROSS-REFERENCE TO RELATED APPLICATIONS

The present application claims the benefit of and priority to U.S. Provisional Patent Application Ser. No. 63/052,571, filed on Jul. 16, 2020, the entire content of which being hereby incorporated by reference.

FIELD

This disclosure relates generally to surgical stapling instruments, and more particularly, to a method for controlling surgical stapling instruments based upon clamping pressure of tissue and to a surgical stapling instrument for performing the method.

BACKGROUND

Anastomosis is the surgical joining of separate hollow organ sections. Typically, an anastomosis procedure follows surgery in which a diseased or defective section of an organ is removed, and the remaining end sections of the organ are joined via a surgical stapling instrument. Depending on the desired anastomosis procedure, the remaining end sections may be joined by circular or side-to-side organ reconstruction methods, for instance.

In a circular anastomosis procedure, the remaining end sections of the organ are joined by means of a surgical stapling instrument which drives a circular array of staples through the remaining end sections and simultaneously cores any tissue interior of the driven circular array of staples to free a tubular passage within the organ. Typically, these surgical stapling instruments include an anvil and a staple cartridge that are moveable in relation to each other between open and clamped positions to clamp the remaining end sections together prior to firing staples to join the end sections together. In the clamped position, the anvil and the staple cartridge are moved to a position defining a predetermined tissue gap. Depending on the thickness of the remaining end sections being clamped, the pressure applied to the remaining end sections will vary greatly. Stapling tissue that is under compressed may lead to blood leaking through a staple line formed by the surgical stapling instrument increasing a likelihood of infection, and stapling tissue that is over compressed may cut off the blood supply to the tissue causing necrosis of the tissue.

A continuing need exists for a stapling instrument that can apply a predetermined clamping pressure to tissue regardless of the thickness of the tissue prior to formation of the staple line in tissue.

SUMMARY

In accordance with the disclosure, a computer-implemented method for controlling a surgical stapling instrument for clamping and stapling tissue to a pressure includes advancing an anvil assembly in relation to a staple cartridge to a first position to define a first tissue gap between the staple cartridge and the anvil assembly that is within a predetermined acceptable range of tissue gaps, measuring a first force of tissue compression of the tissue clamped within the first tissue gap with the anvil assembly in the first position, and entering a firing mode of the surgical stapling instrument if the first force of tissue compression is within a predetermined acceptable range of tissue compression.

In an aspect, the method may further include measuring a second force of tissue compression of the tissue clamped within the second tissue gap that is with the anvil assembly in the second position.

In another aspect, the method may further include entering the firing mode of the surgical stapling instrument if the second force of tissue compression is within the predetermined acceptable range of tissue compression.

In yet another aspect, the method may further include displaying a warning on a display when the second force of tissue compression is not within the predetermined acceptable range of tissue compression.

In an aspect, the method may further include preventing staple firing when the measured second force of tissue compression does not fall within the predetermined acceptable range of tissue compression with the tissue gap within the predetermined range of acceptable tissue gaps.

In another aspect, the predetermined acceptable range of tissue gaps may include a maximum tissue gap and a minimum tissue gap.

In yet another aspect, the method may further include advancing the anvil assembly in relation to the staple cartridge to the minimum tissue gap if the measured first force of tissue compression is not within the predetermined acceptable range of tissue compression.

In still yet another aspect, the method may further include stapling the tissue with the surgical stapling instrument to a target stapling pressure within a predefined stapling pressure range.

In still yet another aspect, stapling the tissue to the target stapling pressure, may include determining if a plurality of staples are present in a reload assembly of the surgical stapling instrument, determining if at least one of a target stapling force is reached or advancing a staple pusher of the surgical stapling instrument to a first staple position is reached, and forming the plurality of staples based on the target stapling pressure In still yet another aspect, the method may further include compensating a stapling stroke of the surgical stapling instrument based on a continuous non-linear backlash loss of a reload assembly of the surgical stapling instrument. Compensating the staple stroke may include adjusting a first staple position and/or a second staple position.

In accordance with the disclosure, a surgical stapling instrument includes an anvil assembly including an anvil head and an anvil center rod extending proximally from the anvil head, a reload assembly including an annular staple cartridge including a plurality of staples, a processor, and a memory. The memory includes instructions stored thereon, which when executed cause the surgical stapling instrument to advance the anvil assembly in relation to the staple cartridge to a first position to define a first tissue gap within a predetermined acceptable range of tissue gaps, measure a first force of tissue compression of tissue clamped within the first tissue gap with the anvil assembly in the first position, and enter a firing mode of the surgical stapling instrument if the first force of tissue compression is within a predetermined acceptable range of tissue compression.

In an aspect, the instructions, when executed, may further cause the surgical stapling instrument to advance the anvil assembly from the first position to a second position to define a second tissue gap within the acceptable range of tissue gaps.

In another aspect, the instructions, when executed, may further cause the surgical stapling instrument to measure a second force of tissue compression of the tissue clamped within the second tissue gap with the anvil assembly in the second position.

In yet another aspect, the instructions, when executed, may further cause the surgical stapling instrument to enter the firing mode of the surgical stapling instrument if the second force of tissue compression is within the predetermined acceptable range of tissue compression.

In still yet another aspect, the instructions, when executed, may further cause the surgical stapling instrument to display a warning on a display when the second force of tissue compression is not within the predetermined acceptable range of tissue compression.

In still yet another aspect, in a case where the measured second force of tissue compression is not within the predetermined acceptable range of tissue compression, and the anvil assembly has advanced past the second tissue gap the instructions, when executed, may further cause the surgical stapling instrument to prevent staple firing.

In still yet another aspect, the predetermined acceptable range of tissue gaps may include a maximum tissue gap and a minimum tissue gap.

In still yet another aspect, in a case where the measured first force of tissue compression is not within the predetermined acceptable range of tissue compression, the instructions when executed, may further cause the surgical stapling instrument to advance the anvil assembly in relation to the staple cartridge to the minimum tissue gap.

In accordance with the disclosure, a non-transitory computer-readable medium storing instructions which, when executed by a processor, cause the processor to perform a method for controlling a surgical stapling instrument for clamping and stapling tissue to a pressure, comprising advancing an anvil assembly in relation to a staple cartridge to a first position to define a first tissue gap within a predetermined acceptable range of tissue gaps, measuring a first force of tissue compression of tissue clamped within the first tissue gap with the anvil assembly in the first position, and entering a firing mode of the surgical stapling instrument if the first force of tissue compression is within a predetermined acceptable range of tissue compression.

BRIEF DESCRIPTION OF DRAWINGS

Systems and methods for controlling surgical stapling instruments for clamping and stapling to a pressure are disclosed herein with reference to the drawings, wherein.

DETAILED DESCRIPTION

Figure 1:
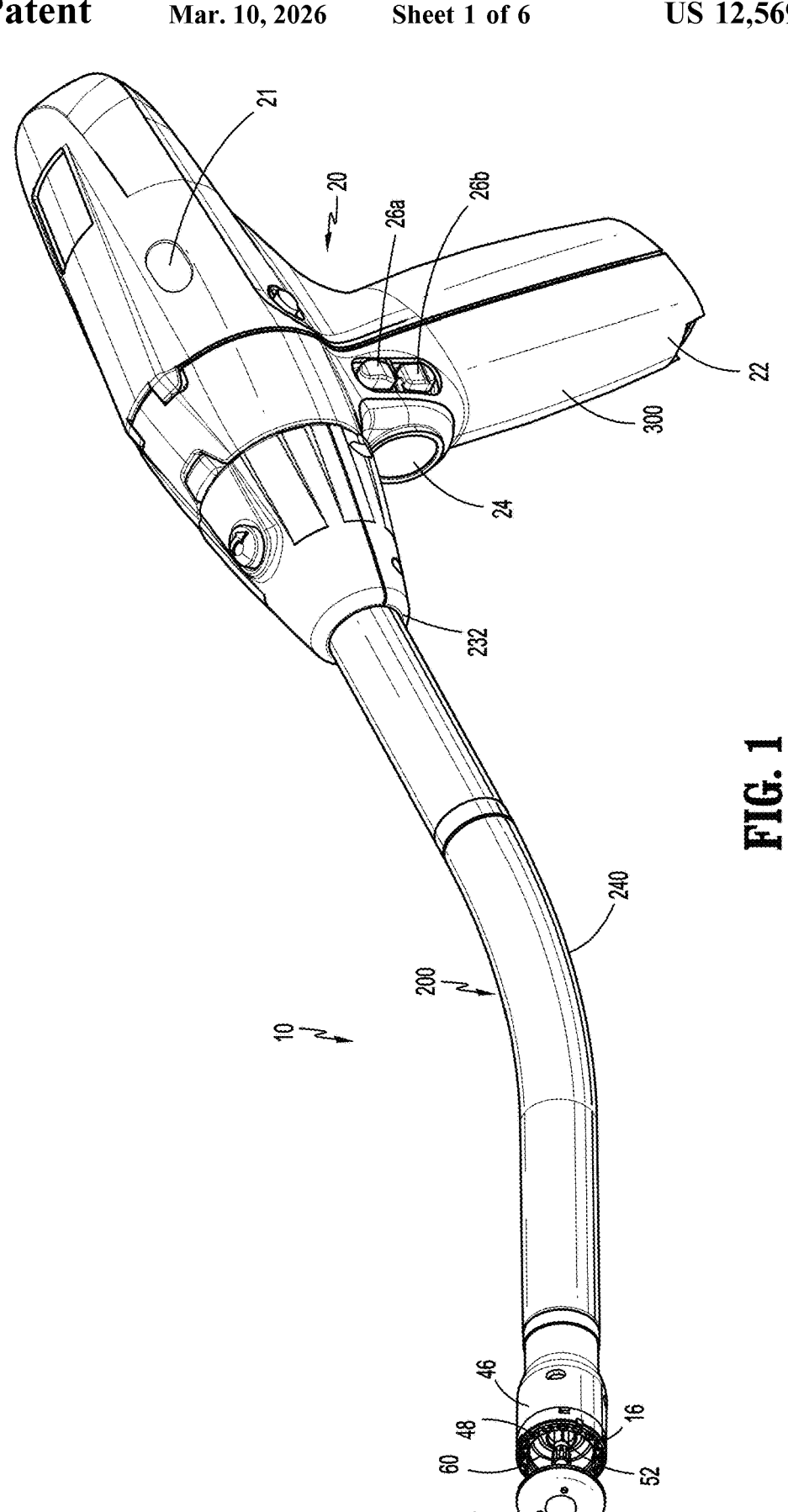
FIG. 1 is a perspective view of a surgical stapling instrument in accordance with the disclosure.

The disclosed surgical device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

This disclosure is directed to a surgical stapling instrument that controls stapling of tissue based in part on the clamping pressure applied to tissue that is clamped between an anvil assembly and a cartridge assembly of the stapling instrument. In aspects of the disclosure, the surgical stapling instrument controls approximation of the anvil and cartridge assemblies to be within a predetermined tissue gap range. The predetermined tissue gap range is selected based upon the size of staples and ensures that the anvil and cartridge assemblies are in close enough proximity to each other that proper staple formation can be achieved. The predetermined tissue gap range includes a maximum tissue gap (in which the tissue gap is the largest within the predetermined tissue gap range) and a minimum tissue gap (in which the tissue gap is the smallest within the predetermined tissue gap range). In order to prevent over compressing tissue within the predetermined tissue gap range which may lead to necrosis of tissue, or under compressing tissue within the predetermined tissue gap range which may lead to blood leakage through a staple line formed by the stapling instrument, the surgical stapling instrument measures the clamping pressure on tissue as the anvil and cartridge assemblies are approximated through the predetermined tissue gap range to ensure that stapling only occurs when the tissue is compressed to a predetermined range of compression. The disclosed surgical stapling instrument and method of use allows the surgical stapling instrument to adjust to tissue thickness, type, and disease to allow more consistent staple formation. Instead of several different stapler sizes being used, the disclosed surgical stapling instrument and method of operation allow for a universal stapler, which reduces stock-keeping units (SKUs) for health care providers. Clamping and stapling to a pressure drives operational efficiencies and saves time during surgical operations. FIG. 1 illustrates a surgical stapling instrument shown generally as surgical stapling instrument 10. The surgical stapling instrument 10 is a circular stapling instrument and includes a handle assembly 20, an adapter assembly 100 that extends distally from the handle assembly 20, a reload assembly 16 that is supported on a distal portion of the adapter assembly 100, an anvil assembly 50 that is operatively coupled to the adapter assembly 100, and a controller 300 (FIG. 3) supported within the handle assembly 20. The reload assembly 16 supports an annular staple cartridge 48 that includes a plurality of staples (not shown). The anvil assembly 50 includes an anvil head 28 that includes a staple forming surface 29 (FIG. 2A).

The handle assembly 20 is illustrated as a powered assembly and includes a stationary grip 22, an actuation button 24 for controlling firing of staples (not shown) from the staple cartridge 48 of the reload assembly 16, and approximation buttons 26a, 26b for controlling axial displacement of the anvil assembly 50 towards and away from the staple cartridge 48 of the reload assembly 16 between open and clamped positions. For a detailed description of the structure and function of exemplary powered handle assemblies, reference may be made to U.S. Patent Application Publication Nos. 2020/0015820 and 2019/0343517. Although the disclosure illustrates a powered assembly, it is envisioned that advantages of the disclosure, as described in detail below, are also applicable to robotically actuated surgical instruments and/or manually operated staplers (e.g., including a pressure sensor that provides an indication that the acceptable clamping pressure has been reached when manual approximation is being performed).

Figure 2A:
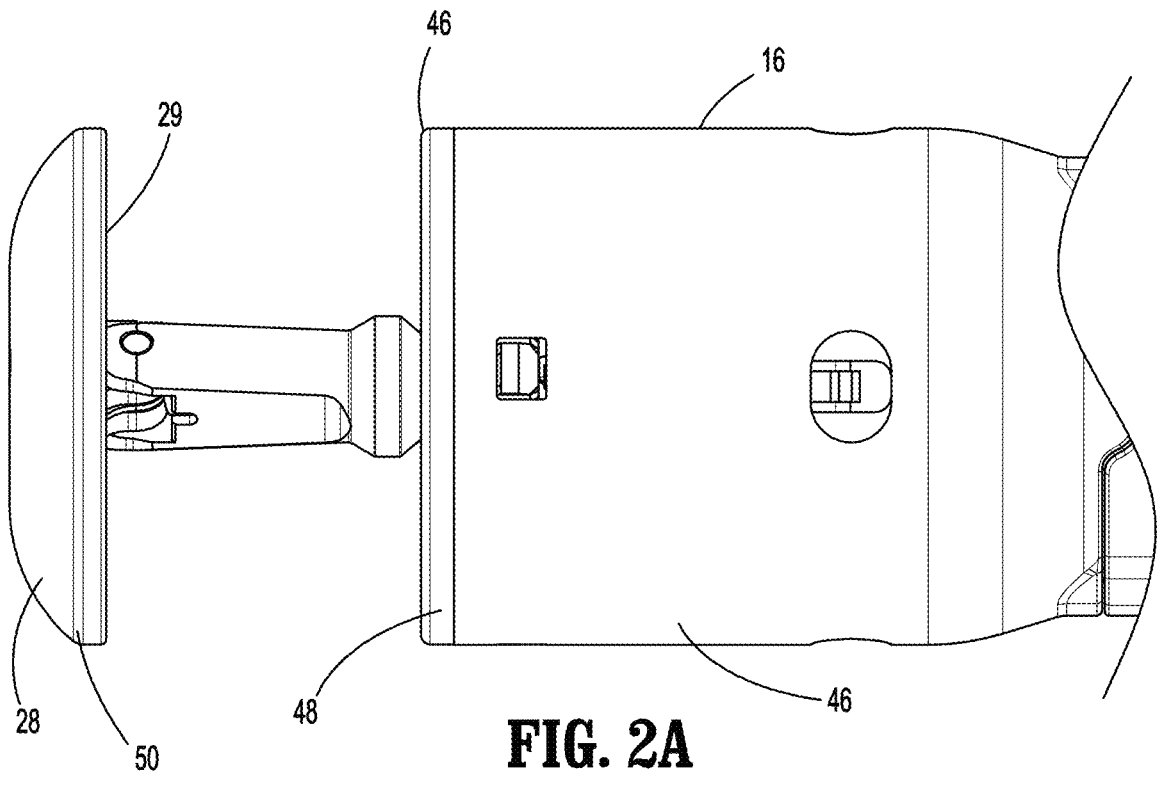
FIGS. 2A-2B are illustrations depicting the surgical stapling instrument of FIG. 1 in the open and clamped positions.
Figure 2B:
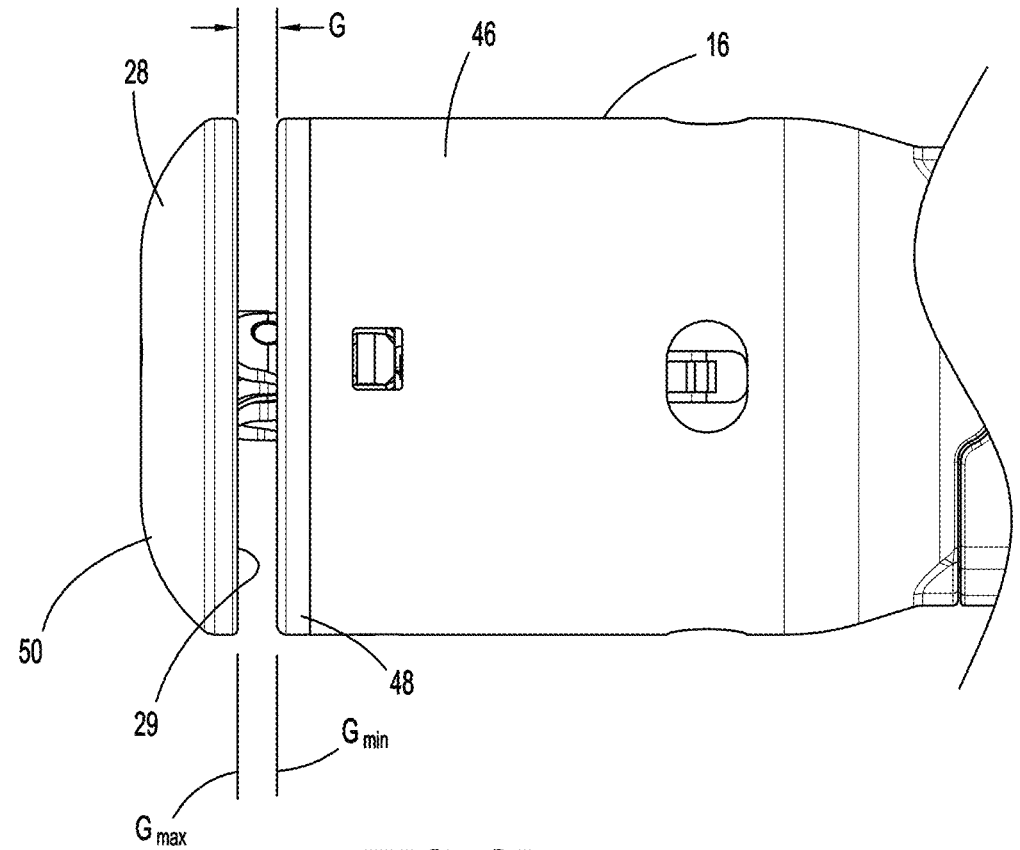

FIGS. 2A and 2B illustrate the surgical stapling instrument 10 in the open and clamped positions. In the open position (FIG. 2A), the anvil assembly 50 is spaced from the staple cartridge 48 of the reload assembly 16 to facilitate placement of tissue between the staple forming surface 29 of the anvil head 28 of the anvil assembly 50 and the staple cartridge 48 of the reload assembly 16. In the clamped position, the anvil assembly 50 is moved into juxtaposed alignment with the staple cartridge 48 to define a tissue gap "G" between the staple forming surface 29 of the anvil head 28 of the anvil assembly 50 and the staple cartridge 48 of the reload assembly 16. In current stapling instruments, both manual and powered, the stapling instruments include a lockout to prevent firing of the stapling instrument unless the tissue gap "G" is within a predetermined range. This predetermined range is determined based in part on the size of the staple being formed and ensures that the anvil head 28 of the anvil assembly 50 is in close enough proximity to the staple cartridge 48 to properly form staples. The predetermined tissue gap range is defined by a maximum acceptable to gap $G_{max}$ and a minimum acceptable tissue gap $G_{min}$.

The handle assembly 20 may include an electrical assembly such as a strain gauge 360 (FIG. 3) that communicates with the controller 300 (FIG. 3) and is configured to determine the load on a motor (not shown) of the surgical stapling instrument 10 resulting from tissue being clamped between the anvil assembly 50 and the staple cartridge 48. This determination can be used to determine a force of compression on the tissue that is clamped between the anvil assembly 50 and the staple cartridge 48.

With continued reference to FIG. 1, the adapter assembly 100 includes an interface portion 232 that is detachably coupled to the handle assembly 20, a tubular shaft 234 that extends distally from the interface portion 232, a drive coupling assembly (not shown) which is movably supported within the adapter assembly 100, and a drive shaft (not shown) that is coupled to an anvil shaft 52 of the anvil assembly 50. The drive coupling assembly (not shown) is engaged with and driven by the handle assembly 20 to control axial displacement of the drive shaft to move the anvil assembly 50 in relation to the staple cartridge 48 between the open and clamped positions.

The reload assembly 16 is supported on a distal portion of the adapter assembly 100 and includes a shell housing 46 that supports the staple cartridge 48. In aspects of the disclosure, the staple cartridge 48 defines annular rows of staple receiving pockets 48a (FIG. 1).

In some aspects of the disclosure, the reload assembly 16 is releasably coupled to the distal portion of the adapter assembly 100 to facilitate the replacement of the annular staple cartridge 48 after each use.

Each of the staple receiving pockets 48a of the staple cartridge 48 supports a staple (not shown) that can be fired from the staple cartridge 48 via actuation of the actuation button 24 of the handle assembly 20. The shell housing 46 of the reload assembly 16 defines an annular cavity 60. The annular cavity 60 supports a staple pusher (not shown) and an annular knife (not shown) which are movable in relation to the staple cartridge 48 to eject the staples from the staple cartridge 48 and to dissect or cut tissue positioned within an annulus defined by the staple cartridge 48. When the staples (not shown) are fired from the staple cartridge 48, the staples are driven into and formed within the staple forming pockets of the staple forming surface 29 of the anvil head 28 of the anvil assembly 50.

Figure 3:
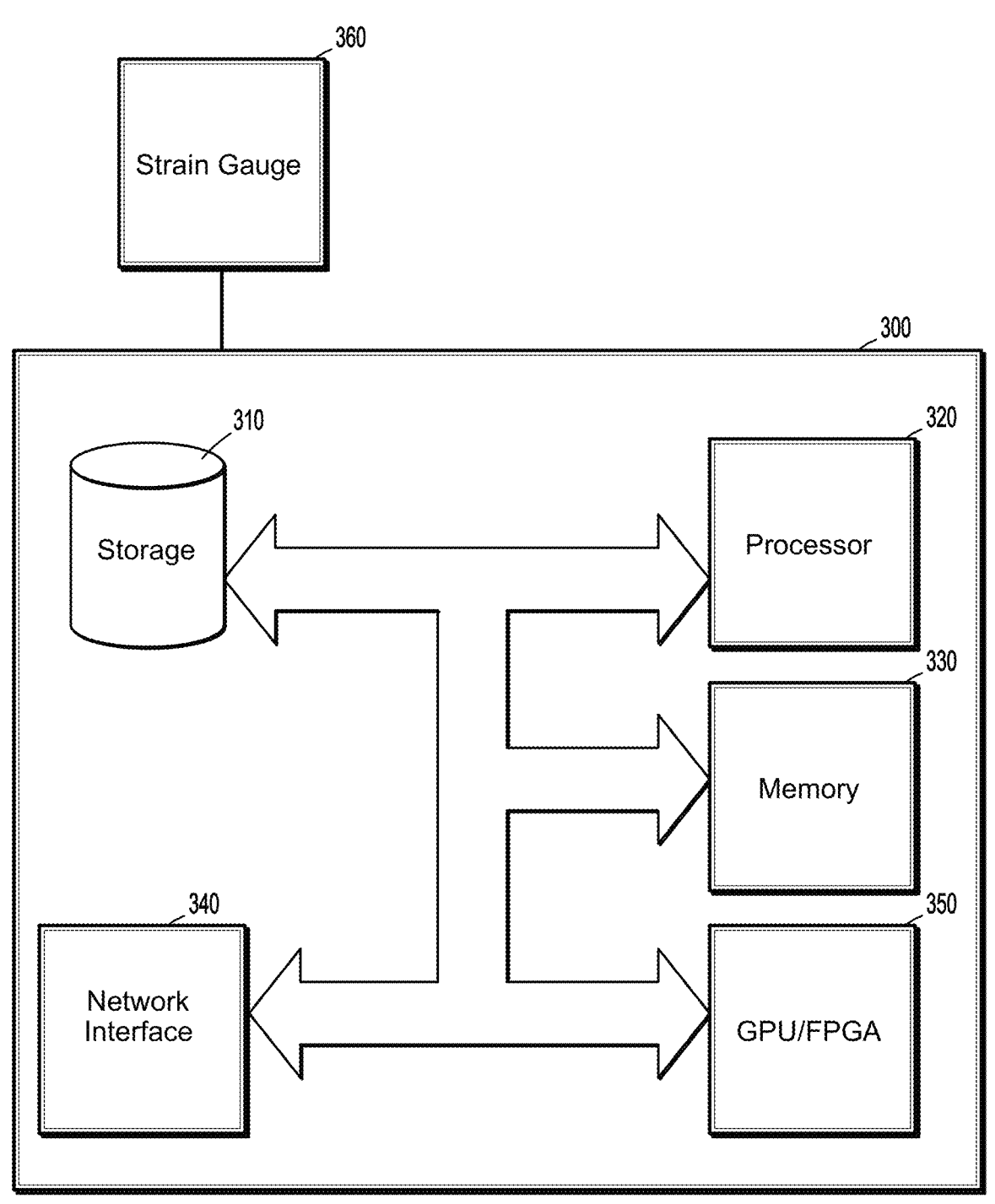
FIG. 3 is a block diagram of a controller provided in accordance with the disclosure and configured for use with the surgical system of FIG. 1.

FIG. 3 illustrates the controller 300, in accordance with the disclosure, which includes a processor 320 that is connected to a computer-readable storage medium or a memory 330. The computer-readable storage medium or memory 330 may be a volatile type memory, e.g., RAM, or a non-volatile type memory, e.g., flash media, disk media, etc. In various aspects of the disclosure, the processor 320 may be another type of processor such as, without limitation, a digital signal processor, a microprocessor, an ASIC, a graphics processing unit (GPU), a field-programmable gate array (FPGA), or a central processing unit (CPU). In certain aspects of the disclosure, network inference may also be accomplished in systems that have weights implemented as memistors, chemically, or other inference calculations, as opposed to processors.

In aspects of the disclosure, the memory 330 can be random access memory, read-only memory, magnetic disk memory, solid-state memory, optical disc memory, and/or another type of memory. In some aspects of the disclosure, the memory 330 can be separate from the controller 300 and can communicate with the processor 320 through communication buses of a circuit board and/or through communication cables such as serial ATA cables or other types of cables. The memory 330 includes computer-readable instructions that are executable by the processor 320 to operate the controller 300. In other aspects of the disclosure, the controller 300 may include a network interface 340 to communicate with other computers or to a server. A storage device 310 may be used for storing data.

In aspects of the disclosure, the strain gauge (not shown) is coupled to the processor, and the disclosed method is run on the controller 300 or on a user device, including, for example, on a mobile device, an IoT device, or a server system.

Figure 4:
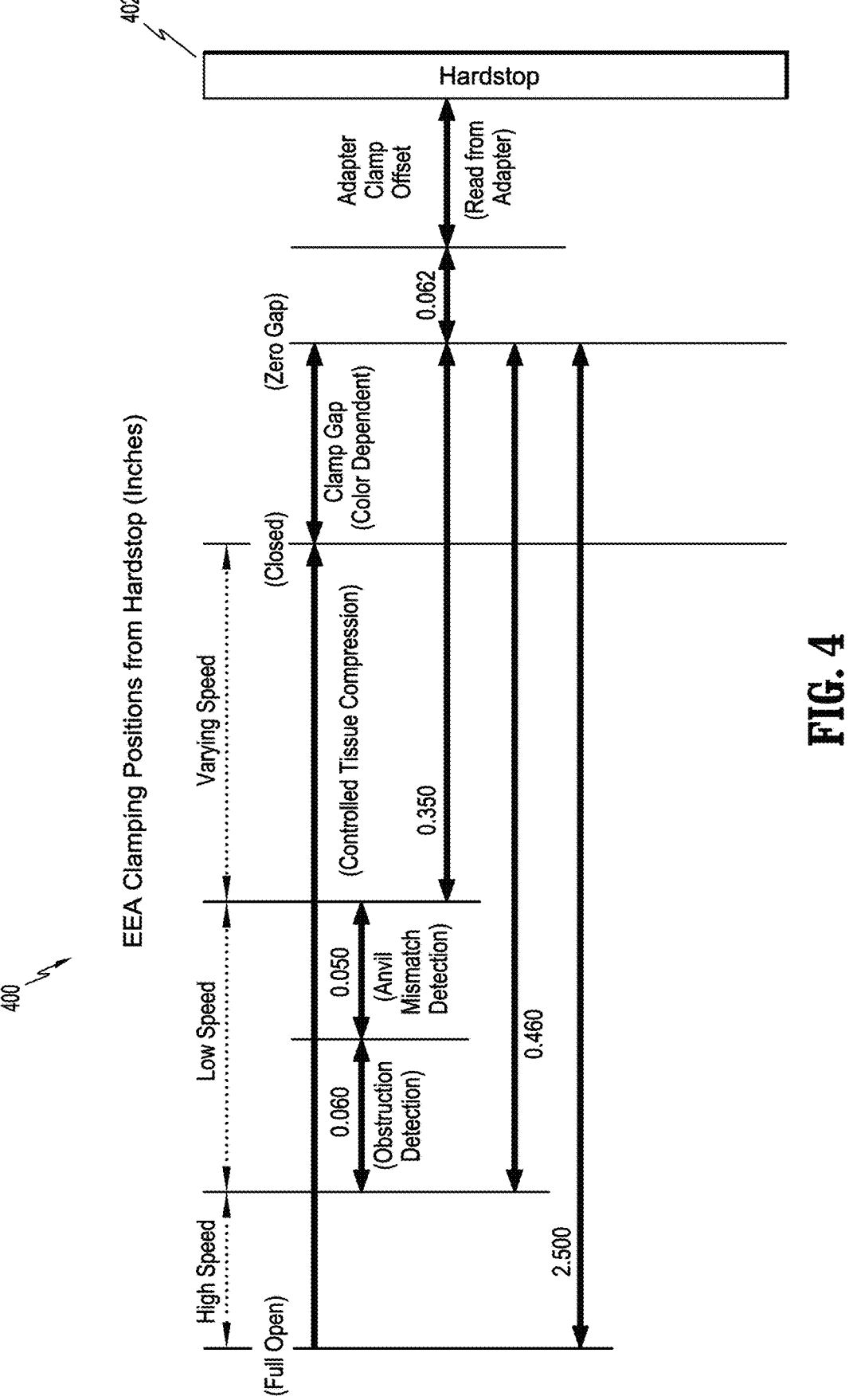
FIG. 4 is an illustration depicting clamping positions from the hard stop of the surgical system of FIG. 1.

FIG. 4 includes an illustration depicting clamping positions from a hardstep of a surgical stapling instrument. The hard stop is a mechanical end stop where a nut on the drive assembly bottoms out on a screw flange. This is achieved by moving each respective function proximally until a torque threshold is achieved.

In stapling instruments, the handle assembly is programmed to advance a drive member through a predetermined stroke to move the anvil assembly 50 from the open position to the clamped position to define a predetermined tissue gap between the staple cartridge 48 and the anvil assembly 50. According to the disclosure, the drive member is controlled by the handle assembly 20 to move the anvil assembly 50 towards the clamped position to compress the tissue clamped between the anvil assembly 50 and the staple cartridge 48 to within a predetermined range of compression. However, the tissue gap "G" (FIG. 2B) must also be within a predetermined range so that proper staple formation can be achieved. The systems and methods of the disclosure implement stapling at a target clamping pressure within a pre-defined range while allowing for clamping to a target minimum force based on adjustable configurable parameters.

Figure 5:
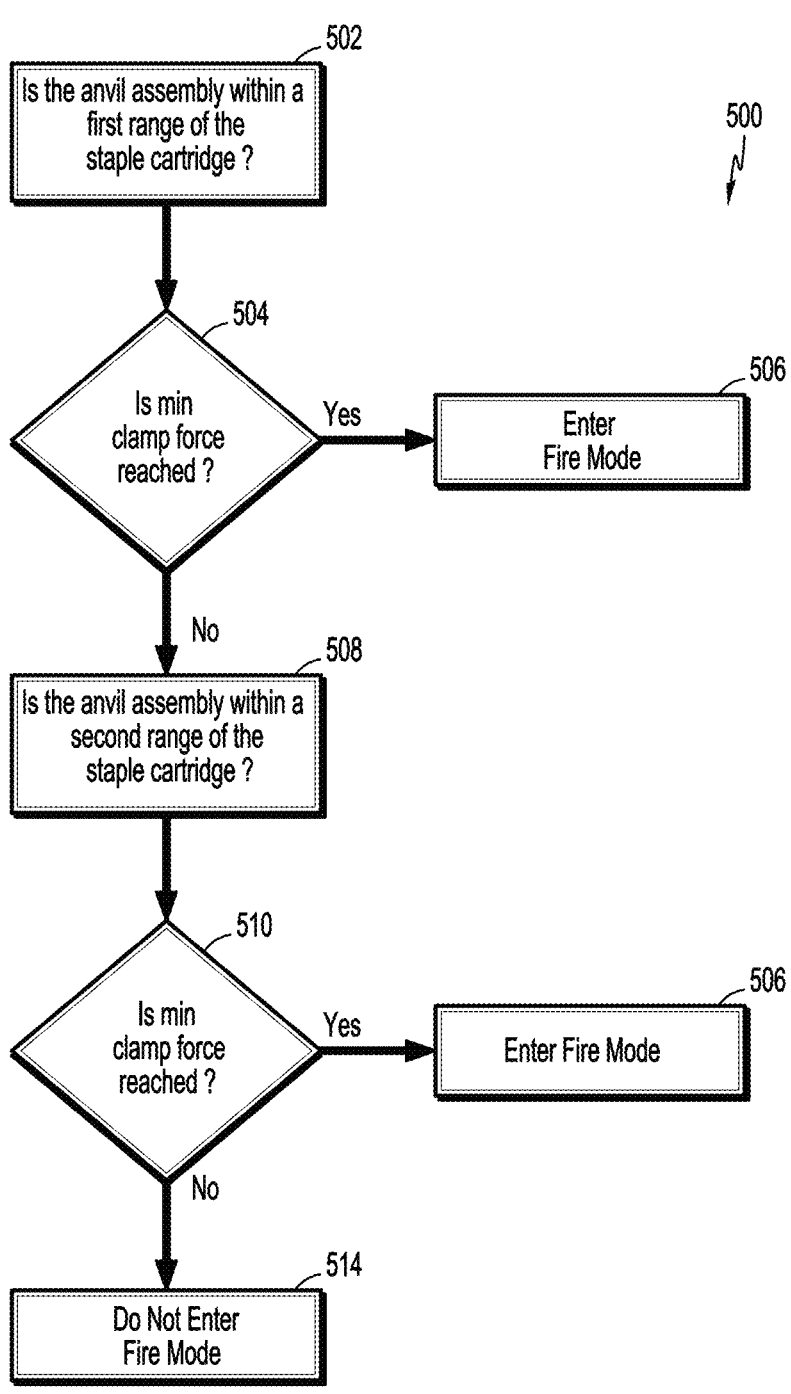
FIG. 5 is a flowchart of a method for controlling a surgical stapling instrument for clamping to a pressure in accordance with the disclosure.

As noted above, it is important that staples are not fired from the staple cartridge 48 into the anvil assembly 50 until the anvil assembly 50 has been moved towards the staple cartridge 48 to define a tissue gap "G" within the predetermined acceptable range of tissue gaps, i.e., between $G_{max}$ and $G_{min}$, wherein $G_{max}$ is the largest tissue gap within the predetermined acceptable gap range, and $G_{min}$ is the smallest tissue gap within the predetermined acceptable gap range. It is also important, for reasons summarized above, that tissue to be stapled is not over compressed or under compressed to provide effective stapling and joining of tissue. Stapling tissue that is compressed to the appropriate degree, i.e., to within a predetermined range of compression, allows the stapling instrument to adjust the amount of staple crimp according to tissue thickness to minimize over compression and under compression of the tissue FIG. 5 illustrates a flow diagram of a computer-implemented method 500 for controlling a surgical stapling instrument for clamping tissue to a pressure within a pre-defined range. The method of forming an end to end anastomosis using the disclosed surgical stapling instrument 10 includes two clamping phases. During a first clamping phase, the anvil assembly 50 (FIG. 1) is moved in relation to the staple cartridge 48 from an open position to a clamped position in which a tissue gap defined between the anvil assembly 50 and the staple cartridge 48 is within a predetermined acceptable gap range to facilitate proper staple formation. More specifically, in the first clamping phase, the anvil assembly 50 is approximated in relation to the staple cartridge 48 of the reload assembly 16 to define the tissue gap of $G_{max}$ (Step 502). In aspects of the disclosure, $G_{max}$ may be from about 0.037 inches to about 0.024 inches. However, the value of $G_{max}$ will vary depending on the size of the staples within the staple cartridge 48.

Once the anvil assembly 50 is moved in relation to the staple cartridge 48 to define the tissue gap of $G_{max}$, a force of tissue compression on the tissue clamped between the staple cartridge 48 and the anvil assembly 50 is measured (Step 504). As discussed above, the clamping pressure of the tissue clamped between the anvil assembly 50 and the staple cartridge 48 of the shell assembly can be measured using a strain gauge 360 that communicates with the controller 300. Alternatively, Other pressure measuring devices may be used to measure the clamping pressure of the tissue clamped between the anvil assembly 50 and the staple cartridge 48. If the compression force on the tissue is within the predetermined acceptable range of compression, the surgical stapling instrument 10 enters the firing mode to allow a surgeon to selectively fire the surgical stapling instrument 10 to staple the tissue (Step 506). The predetermined acceptable range of compression will vary depending on the type of tissue that is being treated.

If a minimum compression force is not found on the tissue in the $G_{max}$ position, the anvil assembly 50 is moved towards $G_{min}$ position (Step 508). As the anvil assembly 50 is moved towards the staple cartridge 48 towards the $G_{min}$ position, the compression force on the tissue is continuously measured. If the compression force on the tissue enters the predetermined range of compression before the anvil assembly 50 reaches the $G_{min}$ position, the surgical stapling instrument 10 enters the firing mode to allow the surgeon to selectively fire the surgical stapling instrument 10 to staple tissue (Step 506). If the anvil assembly 50 reaches the $G_{min}$ position and the compression force on the tissue is not within the predetermined acceptable range of compression, the surgical stapling instrument 10 will not enter the firing mode. As such, the surgical stapling instrument 10 will be prevented from entering the firing mode unless the tissue is clamped to a pressure or force within the predetermined range of compression and the tissue gap "G" (FIG. 2B) defined between the anvil assembly 50 and the staple cartridge 48 is within the predetermined tissue gap range, i.e., from $G_{max}$ to $G_{min}$. In some aspects of the disclosure, the controller may provide a warning on a display 21 on, e.g., the handle assembly 20 of the surgical stapling instrument 10, to alert the surgeon that compression force on the tissue is not within the predetermined range of compression, such that the surgeon can reposition the surgical stapling instrument 10 on the tissue.

Although this disclosure is directed to a powered surgical stapling instrument, it is envisioned the principles of this disclosure are applicable to manually powered stapling instruments. For example, the clamping pressure on tissue clamped between an anvil assembly and a staple cartridge of the stapling instrument can be measured as the stapling instrument is moved through a predetermined acceptable tissue gap range. In such a device, an indicator such as a light can be provided on the instrument. When the clamping pressure of the tissue enters the predetermined acceptable range of compression with the instrument within the predetermined acceptable gap range, the indicator can be activated to notify the surgeon that the instrument is ready to be fired.

It is envisioned that the aspects of this disclosure, although illustrated in association with a circular stapling instrument, are equally applicable to other types of stapling instruments, including linear stapling devices, vessel sealing devices, and other devices for joining tissue sections together.

Persons skilled in the art will appreciate that one or more operations of the method 500 may be performed in a different order, repeated, and/or omitted without departing from the scope of the disclosure. In various aspects, the illustrated method 500 can operate in the controller 300 (FIG. 3), in a remote device, or in another server or system. Other variations are contemplated to be within the scope of the disclosure. The operations of method 500 will be described with respect to a controller, e.g., controller 300 (FIG. 3) of surgical stapling instrument 10 (FIG. 3), but it will be understood that the illustrated operations are applicable to other systems and components thereof as well.

When the surgical stapling instrument 10 is used to conduct a surgical procedure, the surgical stapling instrument 10 is manipulated to position tissue between the staple cartridge 48 and the anvil assembly 50. Once the surgical instrument is properly positioned in relation to the tissue to treat tissue, the handle assembly 20 is actuated to move the anvil assembly 50 towards the clamped position to the Gmm position.

Figure 6:
FIG. 6 is a graph illustrating stapling force vs. staple position of the surgical system of FIG. 1.
Figure 6:
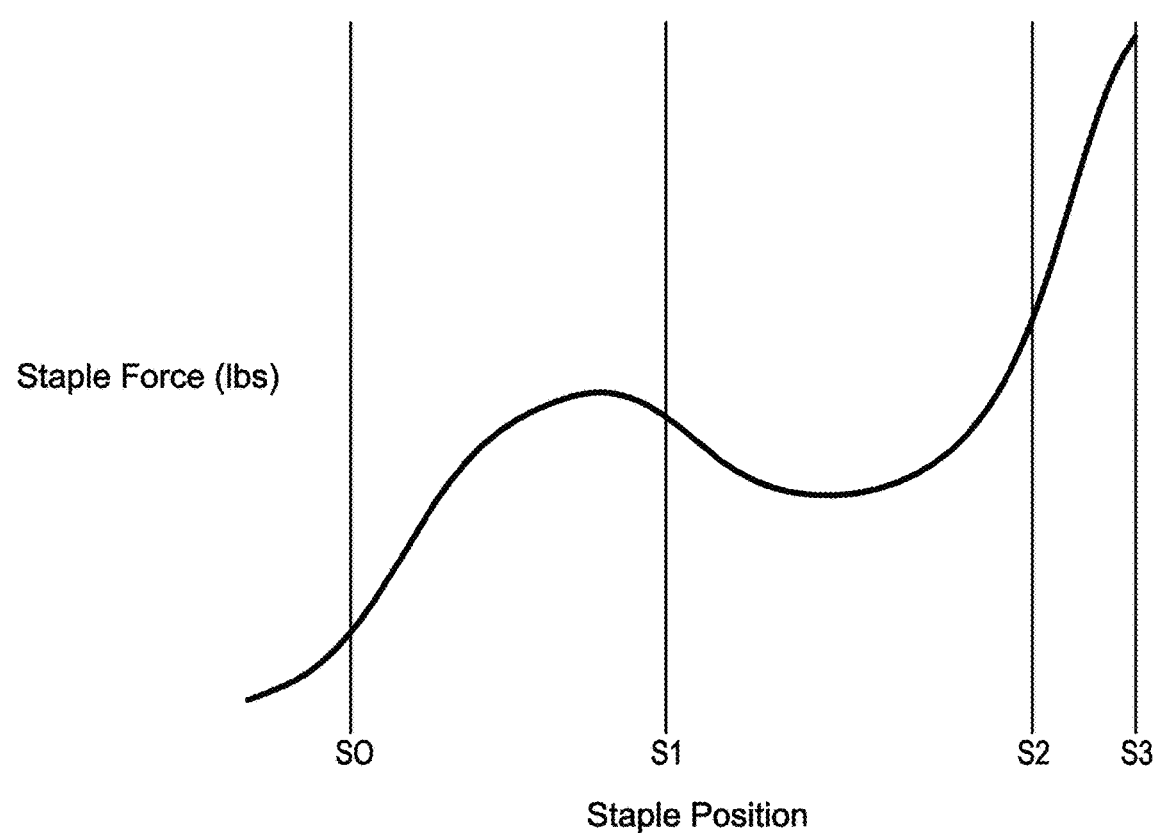

FIG. 6 is a graph illustrating stapling force vs. staple position of the surgical stapling instrument. In aspects of this disclosure, firing staples with the surgical stapling instrument, 10 is done in low speed and has three phases. The first phase is the staple detection process (S0 to S1), in which the software will determine whether staples are present in the staple cartridge 48 of the reload assembly 16. The second phase is the intermediate zone (51 to S2), where the staples contact the anvil assembly 50 and start to bend. The third phase is staple formation (S2 to S3), in which the staples are fully formed and stapling terminates if a predetermined target stapling force is detected between minimum and maximum staple positions.

During the surgery, once an acceptable degree of compression (e.g., the target compression force is reached) within the acceptable staple gap rage (e.g., the predetermined tissue gap range between $G_{max}$ and Gmo, firing of the staples may begin. To fire the staple, the surgeon actuates the actuation button 24 of the handle assembly 20. The method may determine if staples are present in the reload assembly and if so, the method will determine if a target stapling force is reached.

Persons skilled in the art will understand that the instruments and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A surgical stapling instrument comprising:

an annular staple cartridge including a plurality of staples;

an anvil assembly including an anvil head and an anvil center rod extending proximally from the anvil head, the anvil assembly being movable to define a predetermined acceptable range of tissue gaps relative to the annular staple cartridge, the predetermined acceptable range of tissue gaps defining a minimum tissue gap;

a processor; and a memory, including instructions stored thereon, which when executed cause the surgical stapling instrument to:

advance the anvil assembly in relation to the staple cartridge to a first position to define a first tissue gap between the staple cartridge and the anvil assembly that is within the predetermined acceptable range of tissue gaps;

measure a first force of tissue compression of tissue clamped within the first tissue gap with the anvil assembly in the first position; and based on the measured first force being below a predetermined range of compression, further advance the anvil assembly in relation to the staple cartridge to a second position to define a second tissue gap between the staple cartridge and the anvil assembly, wherein the second position is at a minimum gap position corresponding to the minimum tissue gap;

measure a second force of tissue compression of tissue clamped within the second tissue gap when the anvil assembly is in the second position; and based on the second force being less than the predetermined range of compression and the anvil assembly reaching the minimum gap position, prevent entering of a firing mode of the surgical stapling instrument.

2. The surgical stapling instrument according to claim 1, wherein the first tissue gap is a maximum tissue gap of the predetermined acceptable range of tissue gaps.

3. The surgical stapling instrument according to claim 2, wherein the instructions, when executed, further cause the surgical stapling instrument to continuously measure a force of tissue compression as the anvil assembly advances.

4. The surgical stapling instrument according to claim 1, wherein the instructions, when executed, further cause the surgical stapling instrument to display a warning on a display when the second force of tissue compression is not within the predetermined acceptable range of tissue compression.

5. The surgical stapling instrument of claim 1, further comprising a strain gauge, wherein the strain gauge measures the first force and the second force.

6. A surgical stapling instrument comprising:

an annular staple cartridge including a plurality of staples;

an anvil assembly including an anvil head and an anvil center rod extending proximally from the anvil head, the anvil assembly being movable to define a predetermined acceptable range of tissue gaps relative to the annular staple cartridge, the predetermined acceptable range of tissue gaps defining a maximum tissue gap and a minimum tissue gap;

a processor; and a memory, including instructions stored thereon, which when executed cause the surgical stapling instrument to:

advance the anvil assembly in relation to the staple cartridge to a first position to define a first tissue gap between the staple cartridge and the anvil assembly that is within the predetermined acceptable range of tissue gaps;

measure a first force of tissue compression of tissue clamped within the first tissue gap with the anvil assembly in the first position;

based on the measured first force being below a predetermined range of compression, further advance the anvil assembly in relation to the staple cartridge to a second position to define a second tissue gap between the staple cartridge and the anvil assembly, wherein the second position is at a minimum gap position corresponding to the minimum tissue gap;

measure a second force of tissue compression of tissue clamped within the second tissue gap when the anvil assembly is in the second position; and based on the second force being less than the predetermined range of compression and the anvil assembly reaching the minimum gap position, provide a warning to alert a surgeon that the second force on the tissue is not within the predetermined range of compression.

7. The surgical stapling instrument of claim 6, further comprising a strain gauge, wherein the strain gauge measures the first force and the second force.

8. The surgical stapling instrument of claim 6, wherein the first tissue gap is a maximum tissue gap of the acceptable range of tissue gaps.

9. The surgical stapling instrument of claim 6, wherein the instructions, when executed, further cause the surgical stapling instrument to continuously measure a force of tissue compression as the anvil assembly advances.

10. The surgical stapling instrument of claim 6, wherein the instructions, when executed, further cause the surgical stapling instrument to prevent firing when the second force of tissue compression is not within the predetermined acceptable range of tissue compression.

11. The surgical stapling instrument of claim 6, further comprising a handle assembly including a display, wherein the warning is displayed on the display.

12. A surgical stapling instrument comprising:

an annular staple cartridge including a plurality of staples;

an anvil assembly including an anvil head and an anvil center rod extending proximally from the anvil head, the anvil assembly being movable to define a predetermined acceptable range of tissue gaps relative to the annular staple cartridge, the predetermined acceptable range of tissue gaps defining a maximum tissue gap and a minimum tissue gap;

a processor, and a memory, including instructions stored thereon, which when executed cause the surgical stapling instrument to:

advance the anvil assembly in relation to the staple cartridge to a maximum gap position corresponding to the maximum tissue gap;

measure an initial force of tissue compression of tissue clamped at the maximum gap position;

based on the measured initial force being below a predetermined compression force threshold, further advance the anvil assembly in relation to the staple cartridge towards a minimum gap position corresponding to the minimum tissue gap;

as the anvil assembly is advancing, continuously measuring a force of tissue compression and comparing the measured force to the predetermined compression force threshold;

based on the anvil assembly reaching the minimum gap position and the measured force remaining below the predetermined compression force threshold, preventing firing of the surgical stapling instrument; and displaying a warning indicating the measured force is not above the predetermined compression force threshold.

13. The surgical stapling instrument of claim 12, further comprising a strain gauge, wherein the strain gauge measures the force of tissue compression.

14. The surgical stapling instrument of claim 12, further comprising a handle assembly including a display, wherein the warning is displayed on the display.

* * * * *